US006965431B2

(12) United States Patent
Vo-Dinh et al.

(10) Patent No.: US 6,965,431 B2
(45) Date of Patent: Nov. 15, 2005

(54) INTEGRATED TUNABLE OPTICAL SENSOR (ITOS) SYSTEM

(75) Inventors: Tuan Vo-Dinh, Knoxville, TN (US); Alan Wintenberg, Knoxville, TN (US)

(73) Assignee: Ut-Battelle, LLC, Oak Ridge, TN (US)

( * ) Notice: Subject to any disclaimer, the term of this patent is extended or adjusted under 35 U.S.C. 154(b) by 147 days.

(21) Appl. No.: 10/376,965

(22) Filed: Feb. 28, 2003

(65) Prior Publication Data

US 2004/0169854 A1 Sep. 2, 2004

Related U.S. Application Data

(60) Provisional application No. 60/450,837, filed on Feb. 28, 2003.

(51) Int. Cl.[7] .................................................. G01V 3/44
(52) U.S. Cl. ..................................................... 356/301
(58) Field of Search ......................................... 356/301

(56) References Cited

U.S. PATENT DOCUMENTS

| | | | |
|---|---|---|---|
| 4,978,434 A | 12/1990 | Jones et al. | |
| 5,379,065 A | 1/1995 | Cutts | |
| 5,449,907 A | 9/1995 | McKeeman et al. | |
| 5,817,007 A | 10/1998 | Fodgaard et al. | |
| 5,889,900 A | 3/1999 | Hallemeier | |
| 5,891,656 A * | 4/1999 | Zarling et al. | 435/7.92 |
| 5,956,355 A | 9/1999 | Swanson et al. | |
| 6,128,077 A * | 10/2000 | Jovin et al. | 356/310 |
| 6,160,826 A | 12/2000 | Swanson et al. | |
| 6,174,677 B1 | 1/2001 | Vo-Dinh | |
| 6,210,973 B1 * | 4/2001 | Pettit | 436/172 |
| 6,403,947 B1 | 6/2002 | Hoyt et al. | |
| 2003/0016814 A1 | 1/2003 | Vo-Dinh | |

FOREIGN PATENT DOCUMENTS

EP  1236807  9/2002

OTHER PUBLICATIONS

Cullum et al., "Field–portable AOTF–based monitor technology for environmental sensing," Advanced Environmental Sensing Technology II, 4577:65–75, 2002.

Cullum et al., "Development of a Portable Raman Spectrometer for Medical Diagnostics," Biomedical Diagmostic, Guidance, and Surgical–Assist Systems IV, 4615:82–90, 2002.

Vo–Dinh et al., "Surface–enhanced Raman optical data storage: A new optical memory with three–dimensional data storage," Review of Scientific Instruments, American Institute of Physics, 65:3766–3770, 1994.

Cullum, B.; Mobley, J.; Chi, Z.; Stokes, D.; Miller, G.; Vo–Dinh, T., "*Development of a Compact, Handheld Raman Instrument with No Moving Parts for Use in Field Analysis,*" Rev. Sci. Instrum., 71, 1602, (2000).

* cited by examiner

Primary Examiner—Zandra V. Smith
(74) Attorney, Agent, or Firm—Akerman Senterfitt

(57) ABSTRACT

A scanning tunable detection system and related method for analyzing samples includes a source of time varying excitation signals and a tunable optical filter for selectively transmitting time-varying optical signals emanated from a sample following irradiation with the time varying excitation signals. A detector is provided for converting the time-varying optical signals to electrical detection signals. The system can identify components in a sample using phase sensitive or time sensitive detection. A slew scan mode can be used to permit slow scanning through spectral regions rich in information but quickly in regions without such information.

25 Claims, 12 Drawing Sheets

INTEGRATED TUNABLE OPTICAL SENSOR (ITOS) SYSTEM

CROSS-REFERENCE TO RELATED APPLICATIONS

This application incorporates by reference and claims priority to U.S. Provisional Application Ser. No. 60/450,837, filed Feb. 28, 2003, in its entirety.

STATEMENT REGARDING FEDERALLY SPONSORED RESEARCH OR DEVELOPMENT

The United States Government has rights in this invention pursuant to Agreement No. 2051-II18-Y1 between the Federal Bureau of Investigations (FBI) and UT-Battelle, LLC.

FIELD OF THE INVENTION

The invention relates to optical sensors and spectroscopy systems, and more particularly to optical sensors and spectroscopy systems which include tunable filters.

BACKGROUND OF THE INVENTION

Although there has been active research and development regarding sensors, there has been very limited work on integrated systems that combine various features needed for certain practical sensor applications. Integrated senor systems are needed in a wide variety of applications including, medical diagnostics, homeland defense, forensic and investigative, pharmaceutical, food, and agricultural product analysis, environmental bioremediation and monitoring, bioprocess monitoring and biotechnology applications. Unlike fundamental research, portability of instrumentation is an important factor in environmental field monitoring and clinical applications.

Previously disclosed sensor systems have generally relied on commercially available spectrographs equipped with photomultipliers (PMTs) or 2-dimensional detectors, such as charge-coupled device (CCD) based systems, which require bulky electronic and data conditioning accessories. These detector systems required high-voltage power supply systems that often limit these systems for use under field conditions. Besides being bulky, when used in spectroscopy applications these devices limit the available spectroscopic analysis techniques which can be used. For example, phase-sensitive detection is not possible using conventional CCD based systems.

SUMMARY OF INVENTION

A scanning tunable detection system for analyzing a sample includes a source of time varying excitation signals, and a tunable optical filter for selectively transmitting time-varying optical signals emanated from the sample following irradiation with the time varying excitation signals. A detector is provided for converting the time-varying optical signals to electrical detection signals.

The tunable optical filter can comprise an AOTF or a LCTF. The system can include structure for modulating scanning of the AOTF. The system preferably includes a data treatment system for receiving the detection signals, the data treatment system providing at least one of phase-sensitive and time-sensitive detection.

The system can include diffractive optics for dividing a beam from the source of time varying excitation signal into a plurality of discrete excitation light beams. The discrete excitation light beams can irradiate a plurality of locations on the sample. The detector can comprise a detector array including a plurality of pixels for receiving a plurality of said time-varying optical signals emanated from the respective locations on the sample.

The detector can comprise at least one avalanche photodiode, or an array of the same. The system can also include structure for wirelessly transmitting the detection signals.

The time-varying optical signals can comprise Raman signals. The time-varying optical signals can comprise fluorescence signals, phosphorescence signals, or atomic emission signals.

The system can include a gated integrator for receiving the detection signals or signals derived (such as amplified, filtered, etc.) from the detection signals, the gated integrator integrating the detection signals only after a predetermined period of time after the sample irradiation has ceased. A train of pulses can be used to modulate the source of excitation signals, the train of pulses also applied to the gated integrator after the predetermined period of time.

The system can include a synchronous demodulator for receiving the time-varying electrical signals and a phase shift selector, wherein the phase shift selector synchronizes the synchronous demodulator to a modulation frequency applied to the excitation source. In another embodiment, the system can include a synchronous demodulator for receiving the time-varying electrical signals and a phase shift selector, wherein the phase shift selector synchronizes the synchronous demodulator to a modulation frequency applied to an output of the excitation source.

In yet another embodiment, the time-varying excitation signals can comprise a pulse train and the emanated signal can be a series of pulses, wherein the system further comprises a multiplexer for collecting the series of pulses and a first and second counter synchronized with the pulse train. The first counter can process "0" excitation states in the detection signals and the second counter can process "1" excitation states in the detection signals. In this embodiment, a data collection and averaging module can be connected to outputs of both the first and the second counter.

A method for identifying at least one component in a sample includes the steps of providing a source of time-varying radiation, irradiating the sample with said time-varying radiation, wherein a time-varying optical signal emanates from the sample. The time-varying optical signals are then converted to electrical detection signals. The electrical detection signals are processed to provide time-varying measurements relating to the sample. The method can include the step of selectively transmitting time-varying optical signals emanating from the sample, such as using an AOTF or a LCTF. The optical signals comprises Raman signals, or other emanated signals including fluorescence signals, phosphorescence signals, or atomic emission signals.

The time-varying measurements can include lifetime determination or time resolved measurements. The time-varying measurements can include phase resolved measurements.

The method can include the step of slew scanning. In slew scanning, the scanned range can be traversed in a non-constant fashion. Slew scanning permits information rich regions to more closely examined, while regions with little or no desired information can be quickly scanned over.

The method can include the step of delaying initiation of the converting step for a predetermined time after the irradiation. The time-varying source can provide a modulated frequency output, and the method further comprising the step of synchronizing demodulation of said time-varying electrical signals with the modulated frequency. The processing step can comprise imaging the sample.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE PREFERRED EMBODIMENTS

Figure 1:
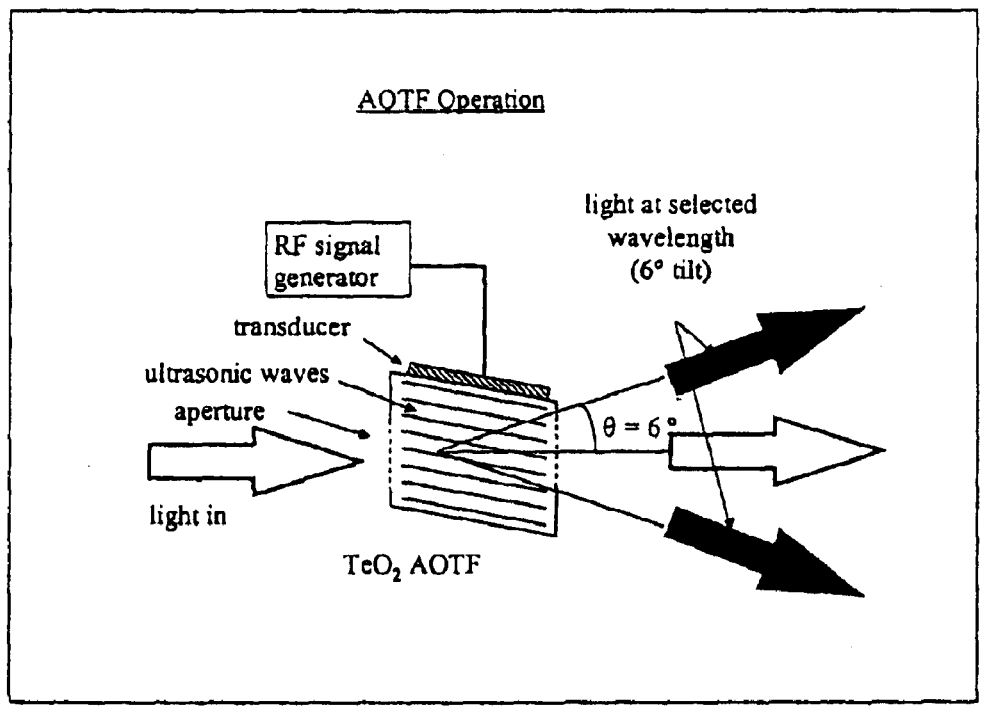
FIG. 1 illustrates operational characteristics of a non-collinear AOTF, where the Bragg grating causes the wavelength of interest to be diffracted off from the rest of the light wavelengths at a slight angle.

The invention includes a sensor system comprising a dynamically tunable band pass optical filter which permits adjustment of transmission bands for selectively passing time varying optical signals emanated from an irradiated sample. A photodetector converts the time-varying optical signals into time-varying electrical signals.

A data treatment system is preferably provided for receiving the electrical signals and providing time-based measurements relating to the sample. The system is referred to herein as an Integrated Tunable Optical Sensor (ITOS) system.

The invention provides significantly improved performance over earlier optical sensor systems by combining several advanced detection and instrumental approaches. Through appropriate signal processing, detectors according to the invention can provide time-resolved measurements and/or phase-resolved measurements. The system can also provide slew scan measurements where the scanned range can be traversed in a non-constant fashion. Slew scanning permits information rich regions to more closely examined, while regions with little or no desired information can be quickly scanned over. Wireless data transmission can be used to transmit the sensor data to one or more remote locations.

The invention can be applied to various spectroscopic detection methods. Although the invention is generally described with respect to Raman spectroscopy, the invention can be practiced with other spectroscopic methods, such as absorption, emissions such as fluorescence and phosphorescence, and elastic scattering.

Raman spectroscopy, which is still an underexploited technique, can provide some significant advantages over other spectroscopic methods for field analysis. Following laser irradiation of a sample, the observed Raman shifts are equivalent to the energy changes involved in transitions of the scattering species and are therefore characteristic of it. These observed Raman shifts correspond to vibrational transitions of the scattering molecule. Such frequencies, when observed using absorption techniques, occur in the infrared (IR) region of the spectrum. Thus, in Raman spectroscopy, the spectrum of interest is in the same spectral region as the excitation radiation, such as laser radiation.

Raman spectroscopy provides more detailed vibrational information, which is often unavailable or unresolvable in fluorescence, UV absorption and reflectance spectroscopy. This information can be related to structural changes in the molecules and to the functions of living tissues and cells. Raman spectroscopy is also more suitable than IR spectroscopy for biological analysis because it does not suffer from the strong IR absorption band of water. The laser wavelength can be selected in the near infrared (NIR) region far away from the water absorption band and where ambient light or room light do not interfere with the detection process. For these reasons, Raman spectroscopy has a great potential for biomedical diagnostics. In spite of these important features, there has been no disclosed spectroscopy system that provides the improved performance needed for sensitive Raman based detection.

The dynamically tunable optical band pass filter can be embodied as a tunable optical dispersion device, such as an Acousto-Optic Tunable Filter (AOTF). One of the inventors has disclosed a basic Raman monitoring using a system based on an AOTF [Ref: B. Cullum, J. Mobley, Z. Chi, D. L. Stokes, G. H. Miller, and T. Vo-Dinh, "Development of a Compact, Handheld Raman Instrument with No Moving Parts for use in Field Analysis," Rev. Sci. Instrum., 71, 1602 (2000)]. An AOTF is a solid-state, electronically tunable bandpass filter which uses the acousto-optic interaction inside an anisotropic medium. The filters can be used with multi-line sources (e.g mixed gas lasers, laser diodes) or with broadband light sources (e.g. xenon, halogen lamps). Tunable band pass filters allow the user to adjustably select and transmit a single wavelength from incoming light that includes a plurality of wavelengths.

The radio frequency (RF) applied to the AOTF transducer controls the transmitted (filtered in 1st order) wavelength. A complete spectrum analysis can be acquired by varying the RF frequency corresponding to the desired wavelength range. The RF amplitude level applied to the transducer controls the transmitted (filtered) light intensity level. This is a unique feature provided by the AOTF. The AOTF has a fast response time, typically being several $\mu$seconds, is accurate, and exhibits a high extinction ratio.

AOTFs offer several advantages over other available optical filters. An AOTF is a compact solid-state device, which has no moving mechanical parts, and an AOTF can be tuned to any wavelength within its operating range in microseconds. In addition, AOTFs are not limited by the small slit size associated with dispersive devices (e.g. grating monochromators). As a result, AOTFs can increase the light intensity throughout the detection using larger apertures. The relevant performance of AOTFs, such as efficiency, bandwidth, and rejection, are compared to that of typical small grating monochromators. AOTF technology offers the multiplex capability to monitor multiple sensors simultaneously at different locations or different samples. The system can also be used to record entire spectral images of samples. These characteristics, combined with the small size of these devices, make AOTFs an important new alternative to conventional monochromators, especially for portable instrumentation in field applications.

In AOTFs a piezoelectric transducer is bonded to a birefringent crystal (typically $TeO_2$ or quartz). The transducer is excited by a RF 50–200 MHz signal and generates acoustic waves in a birefringent crystal. Those waves temporarily establish a periodic modulation of the index of refraction via the elasto-optic effect. Under proper conditions, the AOTF will diffract part of the incident light within a narrow frequency range. This is the basis of an electronically tuned optical filter using the Bragg diffraction of light by periodic modulations in the index of refraction in the crystal established by the acoustic waves. This "phase grating" diffracts only light within a narrow frequency range. The Bragg grating can diffract only light that enters the crystal such that its angle to the normal of the face of the crystal is within a certain range. This range is referred to as the acceptance angle of the AOTF.

Most AOTFs are based on a tellurium oxide ($TeO_2$) crystal. Since it has high acousto-optical figure of merit, $TeO_2$ is the most common material used for AOTFs operating in the visible and near-infrared. However, many compounds of interest exhibit optimal absorption and fluorescence emission peak values in the ultraviolet, and $TeO_2$ is not transparent below 350 nm. In contrast, a collinear-quartz AOTF will be used in this study. In general, non-collinear $TeO_2$ AOTFs can have larger optical apertures than the collinear-quartz type.

In a collinear AOTF the light incident at the optical window in the crystal is linearly polarized. Some of this polarized light is coupled to the diffracted light beam. The polarization of the diffracted (filtered) beam is orthogonal to the incident light. Since the diffracted beam and the incident light beam are collinear, a polarizer at the exit of the crystal separates them.

FIG. 1 illustrates the operational characteristics of a typical non-collinear AOTF, where the Bragg grating causes the wavelength of interest ($\lambda_D$) to be diffracted off from the rest of the light at a slight angle, such as about 6 degrees. The percentage of light diffracted is the diffraction efficiency of the device. This parameter greatly depends on the incidence angle, the wavelength selected and the power of the RF generator signal.

The AOTF spectral resolution, which is defined as the full width at half maximum, $\Delta\lambda$, is given by:

$$\Delta\lambda = \frac{\lambda^2}{2l\Delta n \sin^2\theta_i}$$

where $\lambda$ is the wavelength of observation, $l$ is the interaction length between the acoustic wave and the light wave. $\Delta n = n_e - n_o$; where $n_e$ and $n_o$ are index of refraction of the extraordinary and ordinary axis, respectively, in the anisotropic crystal; while $\theta$ is the incident angle.

An alternative tunable sensor technology is based on liquid crystal tunable filters (LCTF). LCTFs are rapid switching, electronically tuned devices which employ either a ferroelectric or a nematic liquid crystals (LC). The more commonly used nematic LCTF comprises a series of liquid crystal elements whose thicknesses are cascaded in the same way as the Lyot filter. However, the tuning is achieved by electronically rotating the crystal axes of the LC waveplate. When no voltage is applied, the retardance is at a maximum. At large applied voltages, the retardance reaches a minimum. The retardance can be tuned continuously to allow the wavelength to be tuned.

Figure 2:
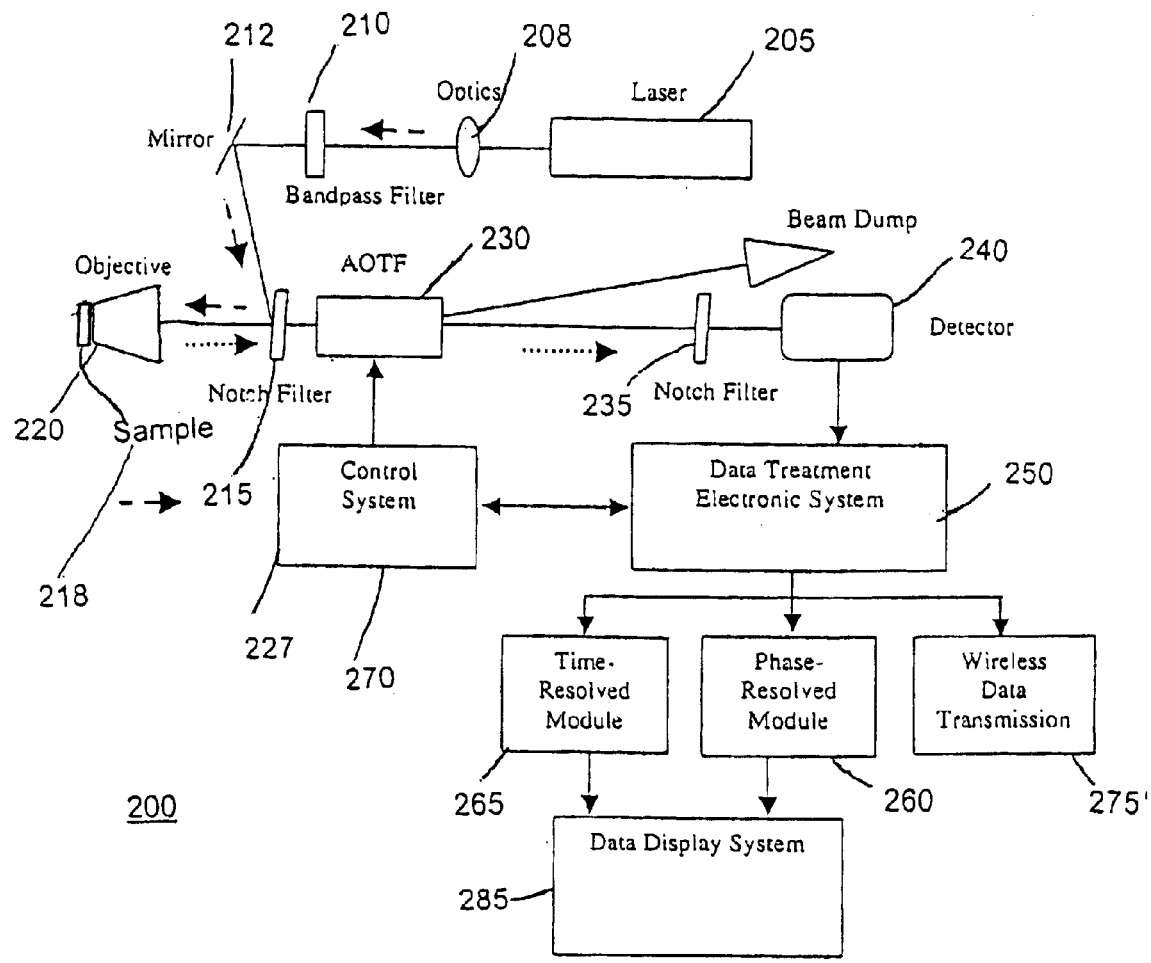
FIG. 2 illustrates a diagram of an integrated optical tunable sensor system, according to an embodiment of the invention.

A schematic of an exemplary ITOS system 200 is shown in FIG. 2. System 200 includes an excitation source 205, such as a HeNe laser or a diode laser. For example, a HeNe laser (Melles Griot, 05-LHR-171, 7 mW at 632.8 nm) or a diode laser (Process Instrument) can be used. Excitation light provided by excitation source 205 is diffracted by optic/focusing lens 208 which can provide a processed excitation light beam. Excitation light passes through bandpass filter 210 and is then reflected off of a reflecting mirror 212 onto a holographic notch filter 215, which again reflects the incident laser light. Notch filter 215 rejects (reflects) a narrow frequency band centered at or near the laser frequency and transmits signals in the rest of the spectrum essentially unchanged.

Although optic/focusing lens 208 is shown providing a single processed excitation beam, optic/focusing lens 208 can provide a plurality of excitation light beams. The respective light beams can have an area to match the area of the respective target areas on the sample being tested to support optional imaging applications The use of the mirror 212 is optional but is desirable to shorten the dimension of the system 200. The excitation light beam is adjusted at an incident angle relative to a surface normal of the notch filter 215 such that over the maximum amount (e.g. 98%) of the incident laser beam is reflected onto the objective. This reflected beam is directed towards a microscope objective 220, such as a 20× microscope objective with a numerical aperture of 0.4 (Nikon, cat. #85502), to be focused to a small area, preferably almost to a point.

To measure a sample 218, the sample 218 is placed just in front of the microscope objective 220 and the backscattered light (e.g. Raman scatter) is then collected and collimated with the same objective 220. This design, which uses the same objective 220 for both excitation as well as collection, allows maximum overlap of the excitation and emission focal volumes to be obtained. Once the scattered light is collimated by objective 220, it passes through the first holographic notch filter 215 (e.g. Kaiser Optical Systems Inc., notch plus-633), which rejects the majority of the Raleigh scattered laser light while allowing the Raman shifted wavelength emanated from sample 218 to be transmitted. Both of the holographic notch filters (215 and 235) used in system 200 preferably provide an optical density of greater than 6.0 for the laser line and maximum transmission, approximately 74%, at 310 $cm^{-1}$ and greater.

For most Raman measurements of organic compounds, 310 $cm^{-1}$ is sufficiently close to the laser line for identification purposes and quantitative analysis. However, holographic notch filters with sharp notch edges, less than 150 $cm^{-1}$, are commercially available and can be used with system 200. Light (e.g. Raman) that is transmitted through the first holographic notch filter 215 is then filtered by a tunable optical filter 230, such as an AOTF (Brimrose, TEAF-0.6-0.9-UH), for wavelength discrimination. The first order diffracted light exiting the AOTF 230 is then passed through a second holographic notch filter 235 to further remove any Rayleigh scattered light and to permit the Raman signal that has passed through the AOTF 230 and focused down onto a detector 240, such as a thermoelectrically cooled photon-counting avalanche photodiode (APD) (EG&G, SPCM-AQ-XY) with a f/1.3 lens.

Bandpass filter 230 can also be an LCTF or other equivalent scanning bandpass filter device. Using a detector 240 that provides 2-dimensional imaging capability, bandpass filter 230 allows ITOS system 200 to provide multi-spectral imaging (MSI) capability or multiplex capability to monitor multiple sensors simultaneously at different locations on a given sample or a plurality of different samples. ITOS system 200 can also be used to record the entire spectral image of a sample.

Assuming bandpass filter 230 is an AOTF, by applying a RF signal to the piezoelectric transducer an acoustic wave is propagated through the crystal. This acoustic wave spatially modulates the refractive index throughout the crystal, which in turn causes only light of a specific wavelength to be diffracted. In the AOTF 230 employed in system 200, the crystal is cut and mounted so that the diffracted wavelength travels along the same path as the incident light while the zero order light is emitted at a six-degree angle with respect to the incident light. This device provides a spectral operating range from 600 to 900 nm. With 632.8-nm excitation the Raman shift will correspond to a large relative wavenumber range (4691.7 $cm^{-1}$).

The detector 240 is preferably an APD-based device. APD-based detectors provide several advantages over other detectors including small size, high quantum efficiency over the wavelength region of interest, and high amplification. Unlike CCDs, APDs can be manufactured using conventional integrated circuit processing, which facilitates integration of APDs with other electronic and optical components on chip. Photodiodes and phototransistors can also be manufactured using conventional integrated circuit processing and can also be used with the invention.

An APD along with all its associated pulse generating electronics can be contained in a single box approximately 4.00×1.25×1.50 inches in size aiding in producing a small final instrument. In addition, APDs are among the most sensitive detectors for the wavelength range of interest. APDs have quantum efficiencies of approximately 70% and due to the inherent nature of APDs, thus reducing the possible added noise when an external amplifier is used. The photon counting APD described above provides a 2 V TTL pulse lasting about 9 ns for every photon detected.

For imaging applications, photodetector 240 can be a detector array comprising a plurality of independent detector pixels (not shown). In this embodiment, as noted above, optic/focusing lens 208 can provide a plurality of discrete excitation light beams, the respective light beams having an area to match the area of the respective target areas on the sample being tested. Each of the respective target areas can be supported by dedicated detector pixels on the detector array. Data display system 285 can provide imaged results using data from the plurality of pixels.

The output of detector 240 is then sent to a data treatment electronic system 250. The data treatment system 250 can comprise a universal counter where the electronic pulses are counted for a specific duration chosen in software. Alternatively, the output of the detector 240 can be sent to various sub-systems comprising data treatment system 250 which can provide various advanced detection modes, such as phase-sensitive detection using phase resolved module 260 or time-sensitive detection using time-resolved module 265. Data display system 285 can display detection data provided by phase resolved module 260 and/or time-resolved module 265.

Figure 7:
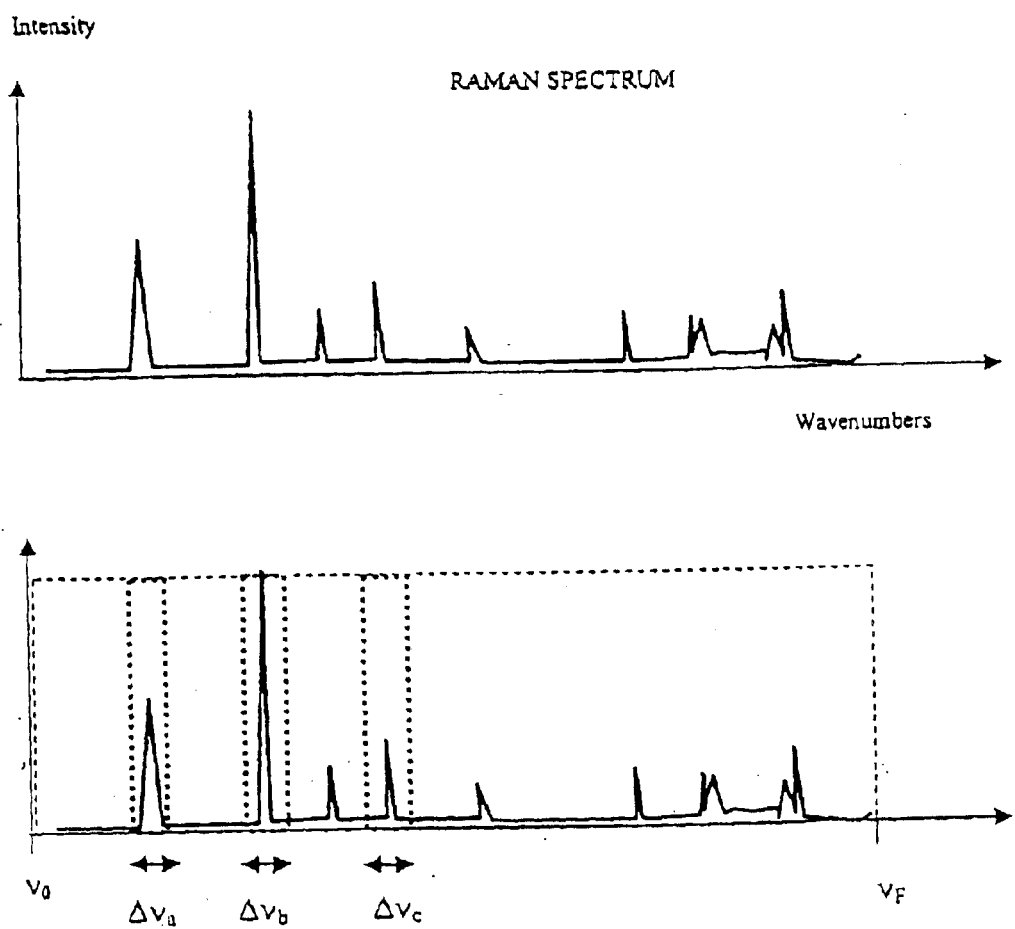
FIG. 7 shows a Raman spectrum showing implementation of slew-scanning for an ITOS system.

Control system 270 can also direct system 200 to operate in a slew scan mode. In the slew scan mode, band pass filter 230 is operated in a non-constant fashion. For example, band pass filter can be scanned slowly through spectral regions rich in information but quickly in regions without such information. FIG. 7, which is discussed in detail later, describes such an embodiment.

Controller 270 can also allow system 200 to implement electronically modulated scanning (EMS). In one embodiment, controller 270 includes an RF signal generator (not shown) for generating and applying a modulated RF signal to AOTF 230. The modulated RF signal modulates the scanning of the AOTF and produces a modulated light output. Modulation of the AOTF scanning provides several advantages. Modulated light output by AOTF 230 can provide a phase-locked detection mode which can improve the signal-to-noise ratio. In addition, light can be modulated around a selected absorption or emission band of interest using this scanning mode.

A wireless data transmission module 275 can also be included with system 200. Transmitter module 275 can include a mixer (not shown) for combining the detection signal with an RF carrier signal, an RF amplifier, transmitter, and antenna (not shown) to permit remote data treatment and analysis. The transmitter can be a transceiver to permit reception of control and other signals from one or more remote sources.

The ITOS system 200 can measure optical signals from a wide variety of spectroscopic processes, including absorption, fluorescence, phosphorescence, elastic scattering, and Raman scattering. One important parameter of the signal emanating from samples of interest is the lifetime of the radiation emanated. The lifetimes of selected various processes are as follows:

(1) absorption: instantaneous with excitation
(2) fluorescence: $10^{-10}$ sec to $10^{-8}$ sec
(3) phosphorescence: $10^{-6}$ to $10^{-3}$ sec
(4) scattering: almost instantaneous with excitation Two methods of measuring emanated signals that permit determination of lifetimes comprise time-resolved and phase-resolved methods. Time-resolved and phase-resolved methods can improve the signal-to-noise values by differencing the actual signal of interest from the background noise (DC signal).

In the time-resolved method, a pulsed excitation signal is used. The width of the excitation is generally much shorter than the emission or other process of interest, so that the excitation width is much shorter than the lifetime (decay time(s)) of the samples. If it is desired to measure the lifetime, the time-dependent emanated intensity I(t) can be measured following the excitation pulse. The decay time $\tau$ can then be calculated from the slope of a plot of log I(t) versus t, or from the time at which the emanated signal intensity (I) decreases to 1/e (about 37%) of the initial emanated intensity value I(t=0).

Figure 3A:
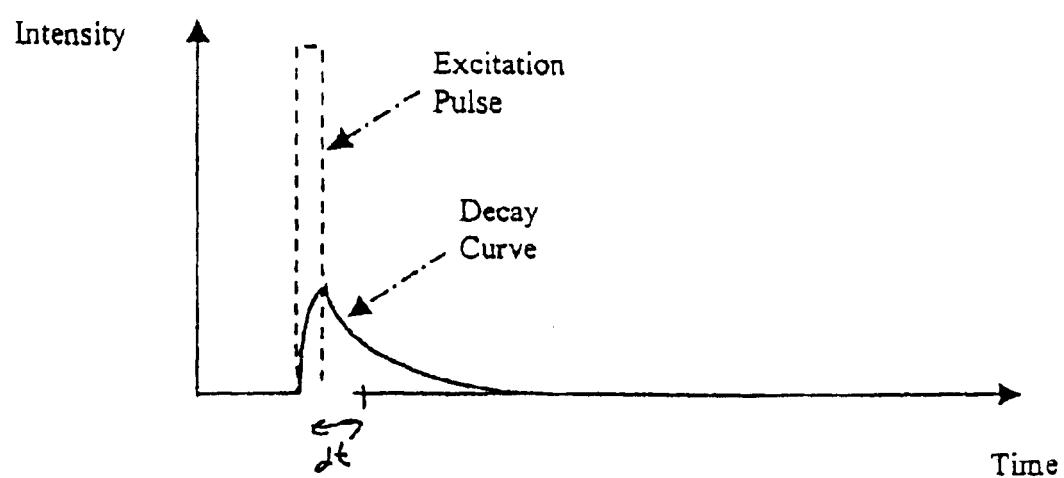
FIG. 3A illustrates an exemplary excitation pulse and the resulting decay curve response provided by a sample.

To measure the emission (or other emanated signal) intensity free from influence from the excitation pulse, the detection process can begin after a delay time (dt) sufficiently after the excitation pulse such that the excitation pulse intensity has decreased close to zero as shown in FIG. 3A. Different compounds generally provide different characteristic decay time(s). Thus, compounds present in samples can be identified on the basis of their decay times.

Figure 3B:
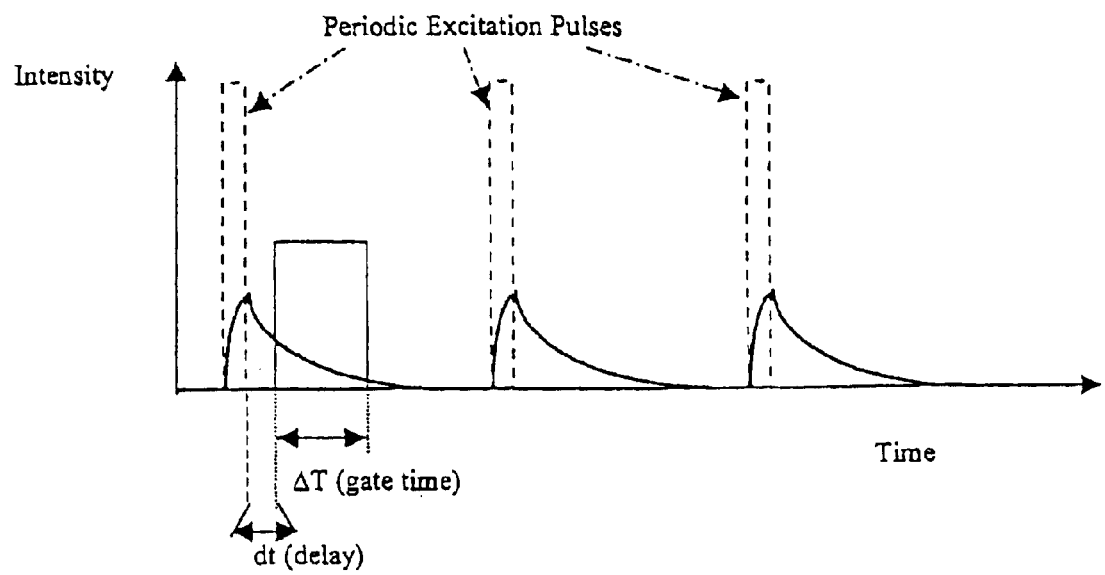
FIG. 3B illustrates a train of periodic excitation pulses and the resulting decay curve responses.

For example, different compounds having different decay times can be differentiated by using different delay times (dT) and gate times (ΔT) as shown in FIG. 3B. The gate time (ΔT) corresponds to the portion of the decay curve in which detection takes place For example, the emission of a compound having a short decay time could be detected using a short gate time, while a longer decay time sample would require a longer gate to properly register (provide a good signal-to-noise value). To distinguish between these two compounds (with only one being present, but not knowing which one), one could perform two measurements using two different (short and long) gate times. If the measurements using two gate times show the same results (same signal intensities), it could be concluded that the compound with the short decay time is present, as all the short-decay emission fits in the two gate windows. However, if the two gate times produce different results (i.e., the signal obtained with the short gate time is lower than the signal with the longer gate time), it could be concluded that the compound present was the one having a long gate time. Similar variations could be performed using a fixed gate time and varying the delay time. A long delay time would cause the measurement to miss short-decay emissions, but register long-decay emissions. A short delay time would register both emissions.

An important source of noise in many measurement situations is the DC noise from the background. Improvement in signal-to-noise can be achieved by using multiple periodic excitation pulses, and by applying the "boxcar" method by integrating the emission signal during a gate time (ΔT) after each pulse as also shown in FIG. 3B.

Figure 4:
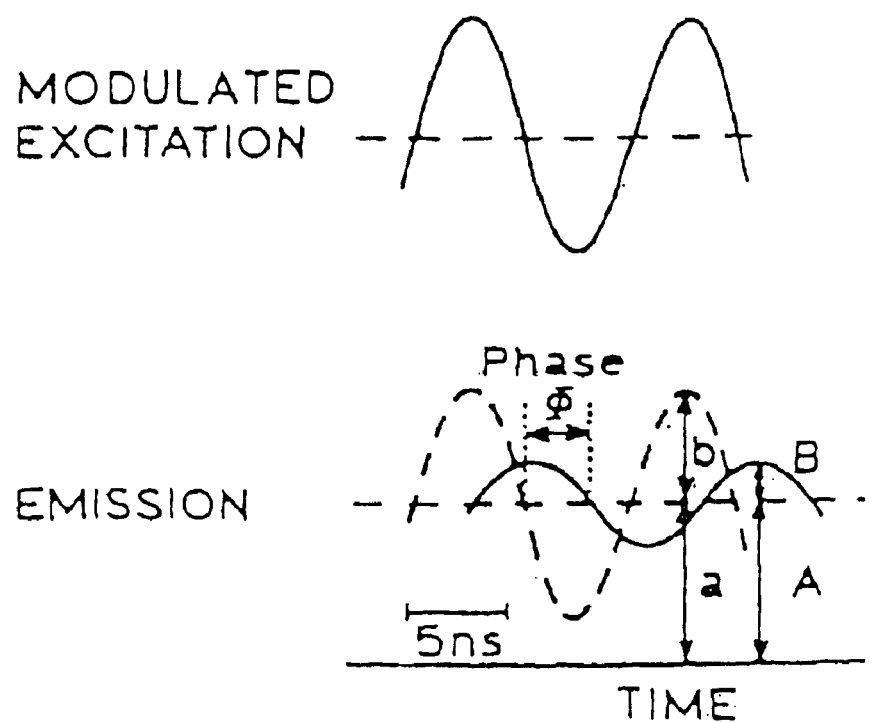
FIG. 4 illustrates a modulated excitation pulse and the resulting modulated emission signal.

Another method that can be used to determine lifetimes involves phase-resolved techniques, which are often referred to as frequency domain techniques. In the phase-resolved technique, the sample is excited with intensity-modulated light. The intensity of the incident light changes with a very high frequency ($\omega=2\pi$ f, f being the frequency in hertz) as compared to the reciprocal of the sample decay time $\tau$. Following excitation with the high frequency modulation signal, the emission or other signal emanation becomes intensity-modulated at the same modulation frequency. However, since the emission or other emanation from the sample follows a decay time, there is a certain delay in the emission relative to the excitation as shown in FIG. 4. This delay is generally measured as a phase-shift ($\phi$), which can be used to calculate the decay time. At each modulation frequency $\omega$, the delay is described as the phase shift $\phi_\omega$, which increases from 0° to 90° with increasing modulation frequency $\omega$.

The finite time response of sample also results in demodulation of the emission by a factor $m_\omega$. This factor decreases from 1.0 to 0 with increasing modulation frequency. At low frequency, the emission or other signal emanated closely follows the excitation signal. Accordingly, the phase angle is near zero and the modulation is near 1. As the modulation frequency is increased, the finite lifetime of the emission or other emanation process prevents the emission from closely following the excitation. This results in a phase delay of the emission, and a decrease in the peak-to-peak amplitude of the modulated emission or other signal emanated.

The shape of the frequency response is determined by the number of decay times displayed by the sample. If the decay is a single exponential, the frequency analysis is simplified in this case, the phase angle or modulation at any frequency can be used to calculate the lifetime. For single-exponential decay, the phase and modulation are related to the decay time ($\tau$) by the following relations:

$$\tan \phi_\omega = \omega\tau; \text{ and } m_\omega = (1+\omega^2\tau^2)^{-1/2}$$

Therefore, one can differentiate and thus identify various emissions or other signal emanations having different decay times by selecting the phase shift ($\phi$) optimized to the decay time ($\tau$) of interest. This method is generally referred to phase-resolved detection.

Figure 5A:
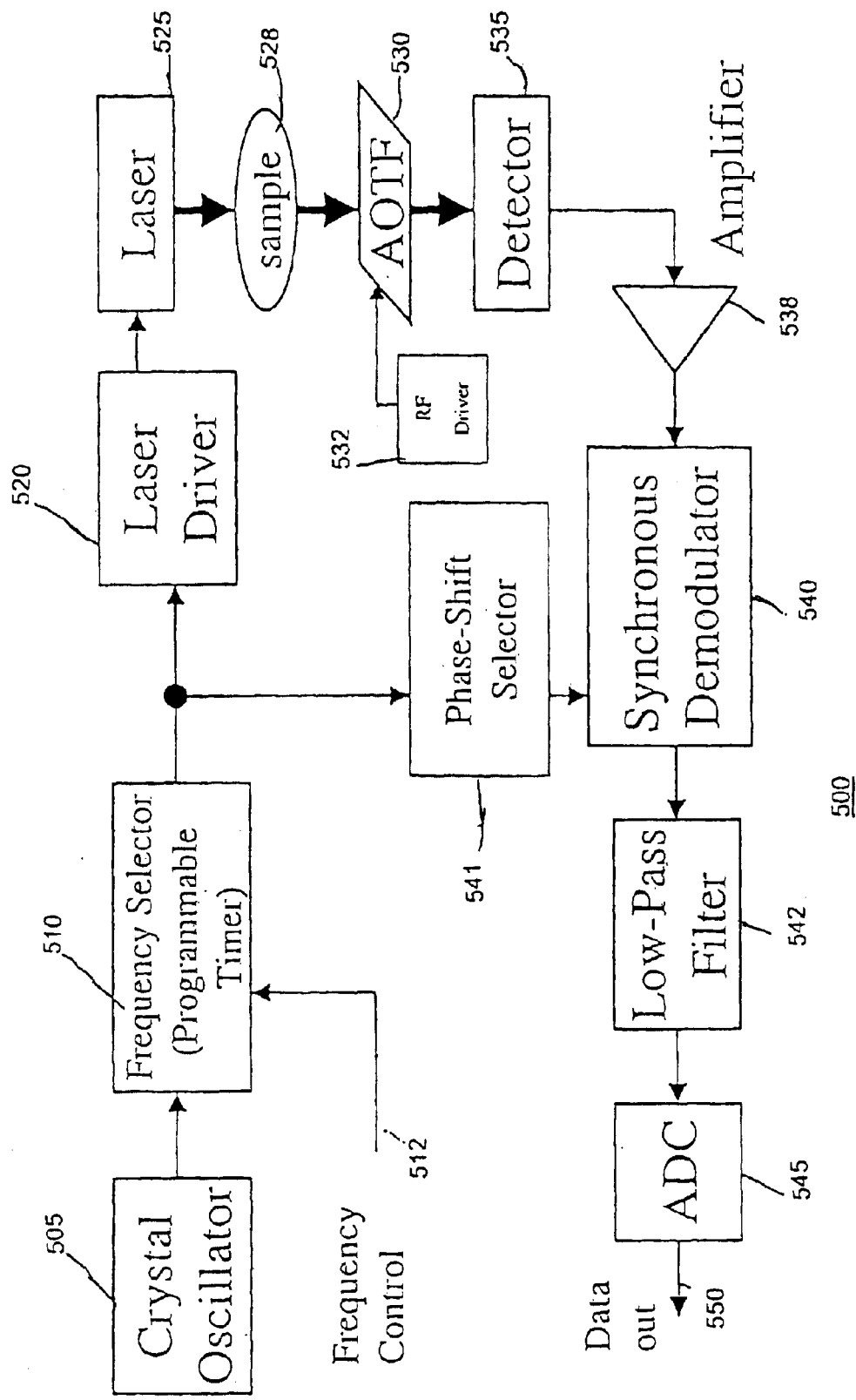
FIG. 5A is a block diagram of a modulated excitation and synchronous detection system which utilizes analog demodulation.

FIG. 5A illustrates an ITOS system 500 which includes a modulated excitation source and synchronous detection using analog intensity modulation. A crystal oscillator 505 provides a modulation frequency to a frequency selector 510 (e.g. programmable timer) which is driven by a frequency control 512, which selects the frequency used to run laser driver module 520, which drives laser 525. The laser driver 520 modulates the intensity of the laser light emitted by laser 525, which is used to excite the target sample 528. The laser 525 can be modulated, such as 50% on-time and 50% off-time. The Raman signal (or other signal emanated, such as fluorescence, phosphorescence) is band pass filtered by a band pass filter, such as AOTF 530, which is driven by RF driver 532.

AOTF 530 isolates the emission or other signal of interest from other interferences, such as laser scattered light and background noise. Assuming Raman detection is desired, the isolated Raman signal is detected by detector 535, such as an avalanche photodiode (ADP) or a photomultiplier (PMT), or an array of the same, which converts the emanated signal (e.g. Raman signal) into an electrical signal.

Output current provided by detector 535 (e.g. APD) is amplified using an amplifier 538 having sufficient bandwidth to pass the excitation frequency, since the excitation signal is also used as the phase input to the synchronous demodulator 540. The synchronous demodulator 540 is operated by a phase-shift selector 541, which is synchronized with the laser excitation modulation frequency. This arrangement synchronously rectifies the output provided by amplifier 538. A low-pass filter 542 is used to average the output of the synchronous demodulator 540. To the first order, any signal not having the same frequency as the excitation frequency is averaged to zero, so this approach rejects dc and other interference signals. The output of low pass filter 542 is then provided to analog-to-digital converter (ADC) 545, which provides a digital data output 550.

The finite time response of the sample also results in demodulation of the emission or other emanated signal by a factor $m_\omega$. As noted earlier, for single-exponential decay, the phase and modulation are related to the decay time ($\tau$) by tan $\phi_\omega = \omega\tau$ and $m_\omega = (1+\omega^2\tau^2)^{-1/2}$. Therefore, for Raman, fluorescence and phosphorescence detection, various emissions or other emanated signals having different decay times can be differentiated by selecting a phase shift ($\phi$) optimized to the decay time ($\tau$) of interest (phase-resolved detection). The phase-resolved technique is also helpful for distinguishing the modulated signal emanated from the sample (e.g. Raman signal) from the dc background signal, such as signals from sun light or room light.

Figure 5B:
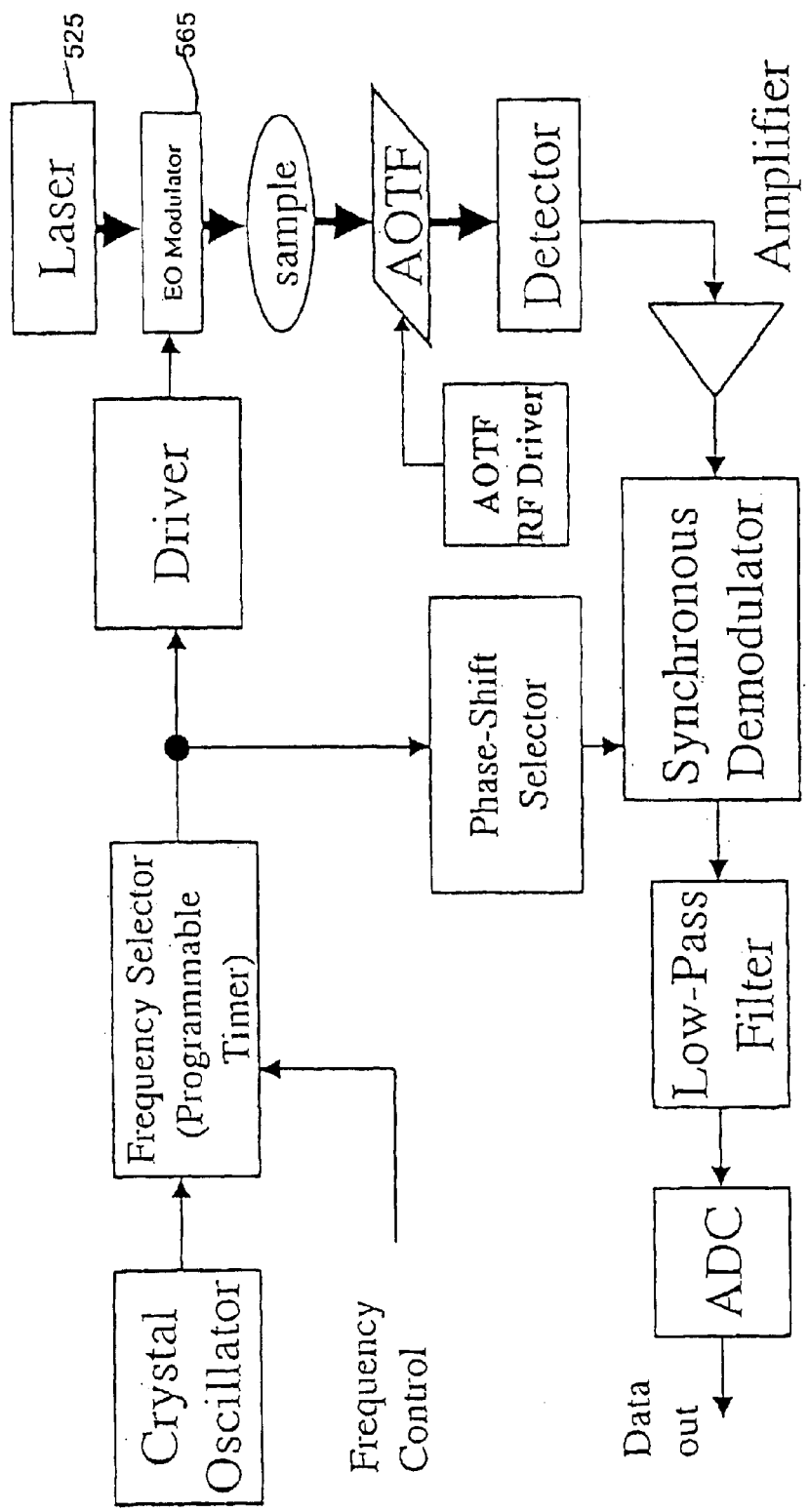
FIG. 5B is a block diagram of a modulated excitation and synchronous detection system which utilizes analog demodulation and includes an electrooptic modulator.

FIG. 5B shows an ITOS system 560, which closely parallels system 500 shown in FIG. 5A. System 560 is also adapted for phase-resolved detection. Rather than directly modulating laser 525 in system 500, system 560 modulates the output of laser 525 by applying a modulating signal, such as to electro-optic modulator 565 (e.g. Pockels cell) or other light modulator to modulate the laser excitation light. System 560 can provide advantages over system 500 in certain system arrangements. For example, some lasers may not be physically able to be modulated as shown in system 500, or if they are, their frequency or amplitude stability may be compromised.

Figure 5C:
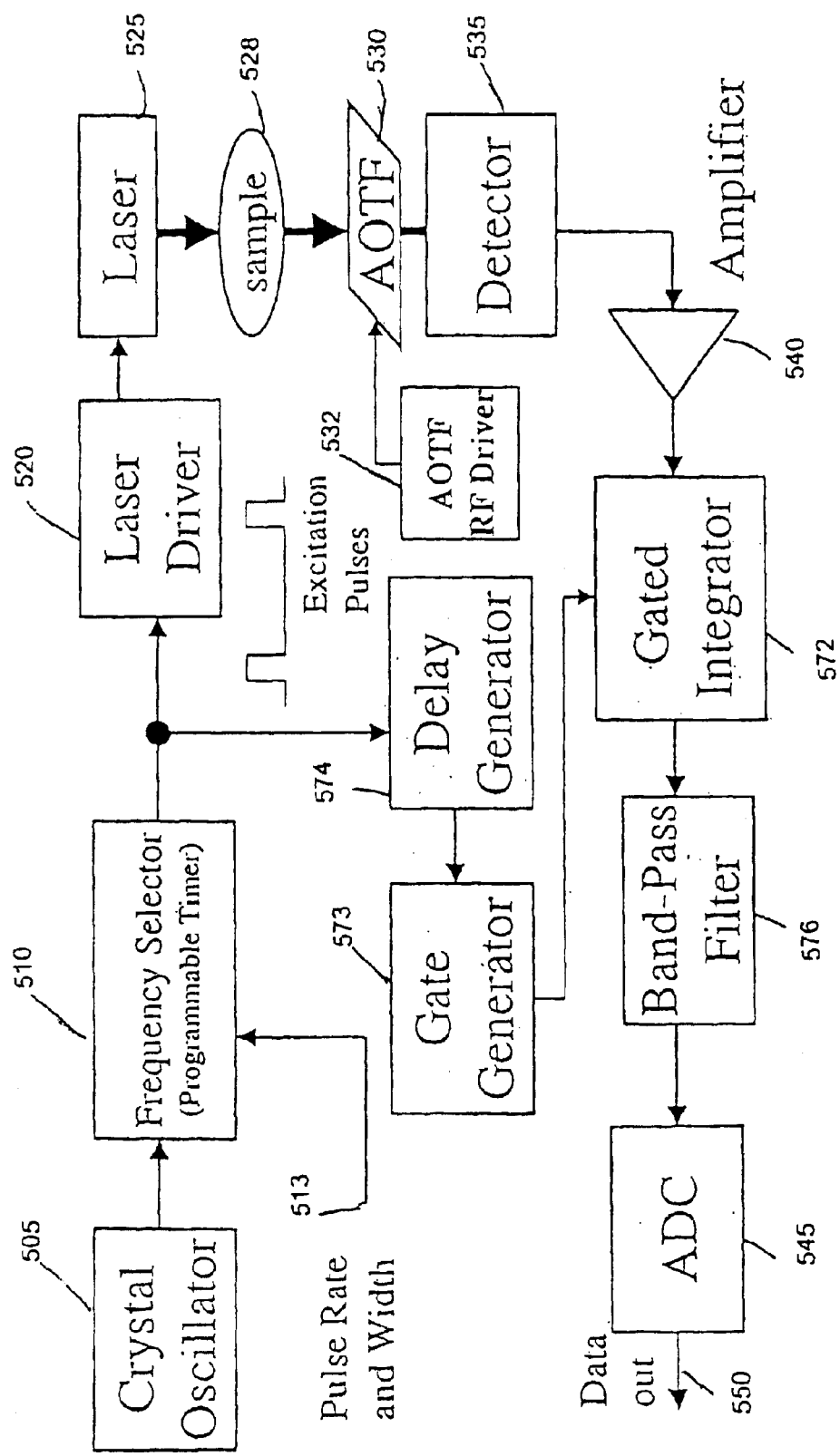
FIG. 5C is a block diagram of a pulsed excitation and gated detection system utilizing analog gated integration.

FIG. 5C shows an ITOS system 570 with pulsed excitation and gated detection using analog gated integration. An oscillator (such as a crystal oscillator) 505 provides the modulation frequency to a frequency selector 510 (e.g. programmable timer), which selects the frequency used to run laser driver module 520 using inputs from pulse rate and pulse width control 513. The laser driver module 520 triggers pulses from laser 525 used to excite the target sample 528. The resulting Raman (fluorescence, or other) signal emanated from the sample is detected via a tunable optical filter, such as AOTF 530, which is used to isolate the Raman or other emanated signal from other interferences (e.g., laser scattering, background noise). The isolated emanated signal is detected by detector 535 (e.g., APD), which converts the optical signal into an electrical signal. The electrical signal is amplified by the amplifier 540 and then fed to gated integrator 572.

The gated integrator 572 opens "the detection gate" to process detection signal data only when it receives a signal from a gate generator 573, which is triggered by a delay generator 574. The delay generator is preferably driven by the same excitation pulses output by frequency selector 510 that triggers laser driver 520, but set a time delay (dt) between the excitation pulses and the opening of the detection gate as shown earlier in FIG. 3B. Therefore, it is possible to eliminate influence from laser scatter by setting a sufficient time delay (dt) delay period.

Alternatively it is possible to decrease the fluorescence background from the Raman or other signal of interest. For example, fluorescence emission from the background which generally has different decay times τ can also be discriminated from the Raman signal of interest by using different time delay (dt) values optimized to the target probe decay times.

The signal from the gated integrator 572 is then fed into a bandpass filter 576 and then preferably to a power averaging circuit (not shown). Finally the analog signal is fed into an analog-to-digital converter (ADC) 545, which provides a digital data output 550 which represents the detection signal.

Figure 6A:
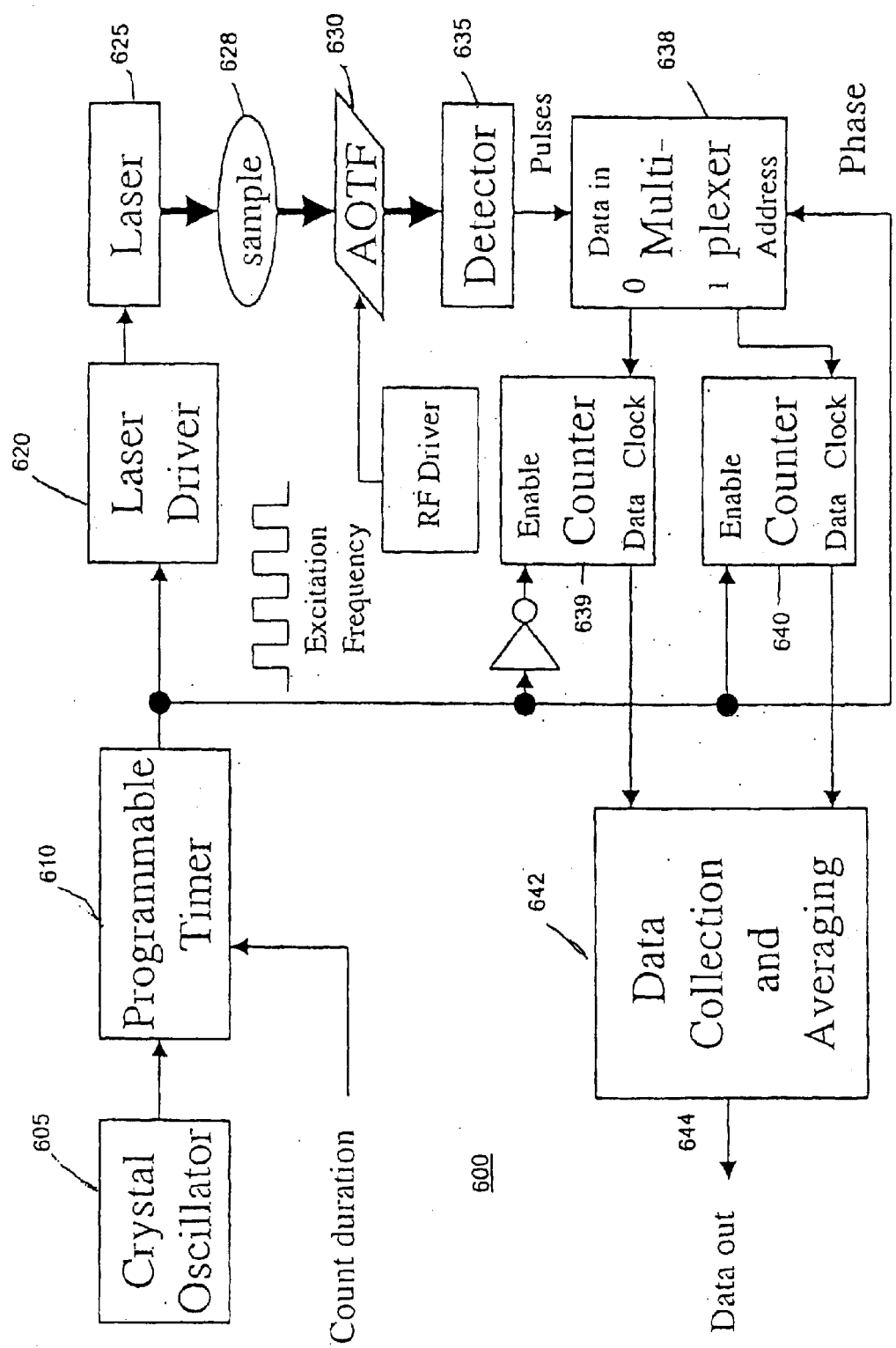
FIG. 6A is a block diagram of a modulated excitation and synchronous detection system using digital demodulation.

FIG. 6A shows an ITOS system 600 with modulated excitation and synchronous detection using digital demodulation. An oscillator (such as a crystal oscillator) 605 provides a base frequency to a frequency selector 610 (e.g. programmable timer), which generates the modulation frequency used to run laser driver module 620. The laser driver 620 modulates the intensity light from laser 625 which is used to excite the target sample 628. The Raman signal (or, e.g. fluorescence, phosphorescence) is detected via an AOTF or similar band pass filter 630, which is used to isolate the emission or other detection signal from other interferences (e.g., laser scattering, background noise). The isolated Raman (fluorescence) emission is detected by the detector 635 such as an avalanche photodiode (ADP) or a photomultiplier (PMT), which converts the luminescence signal into an electrical signal. The detector should include electronic circuits to produce pulses from the detected Raman (luminescence) signal. Alternatively, the electrical signal from the detector can be amplified by an optional amplifier, and then passed to a comparator or discriminator to produce pulses (both not shown in FIG. 6A).

The laser light is modulated, such as using a 50% duty cycle pulse provided by laser driver 620. Accordingly, the signal emanated from the sample which is detected by detector 635 (e.g. APD) is in digital form (a series of logic pulses with nearly a 50% duty cycle). The pulses are collected in a multiplexer 638, and then fed to two counters. For example, counter 639 can provide processing for "0" excitation states and counter 640 for processing "1" excitation states. The on/off cycles of the two counters 639 and 640 are synchronized with the excitation/detection cycle by enabling each with the same modulated excitation waveform provided by laser driver 620 which drives laser 625. For example, counter 639 can be enabled when the laser excitation cycle is off, and thus can provide the background signal. The other counter 640 is enabled when the laser excitation cycle is on, and thus provides the signal emanated from sample 628. The delay time of the counter cycle can be varied in order to perform phase-resolved measurements. The digital signals from both counters 639 and 640 can be fed into a data collection and averaging module 642, where the detection signal can be processed (e.g., background subtraction, etc) before being output as digital data out 644.

Figure 6B:
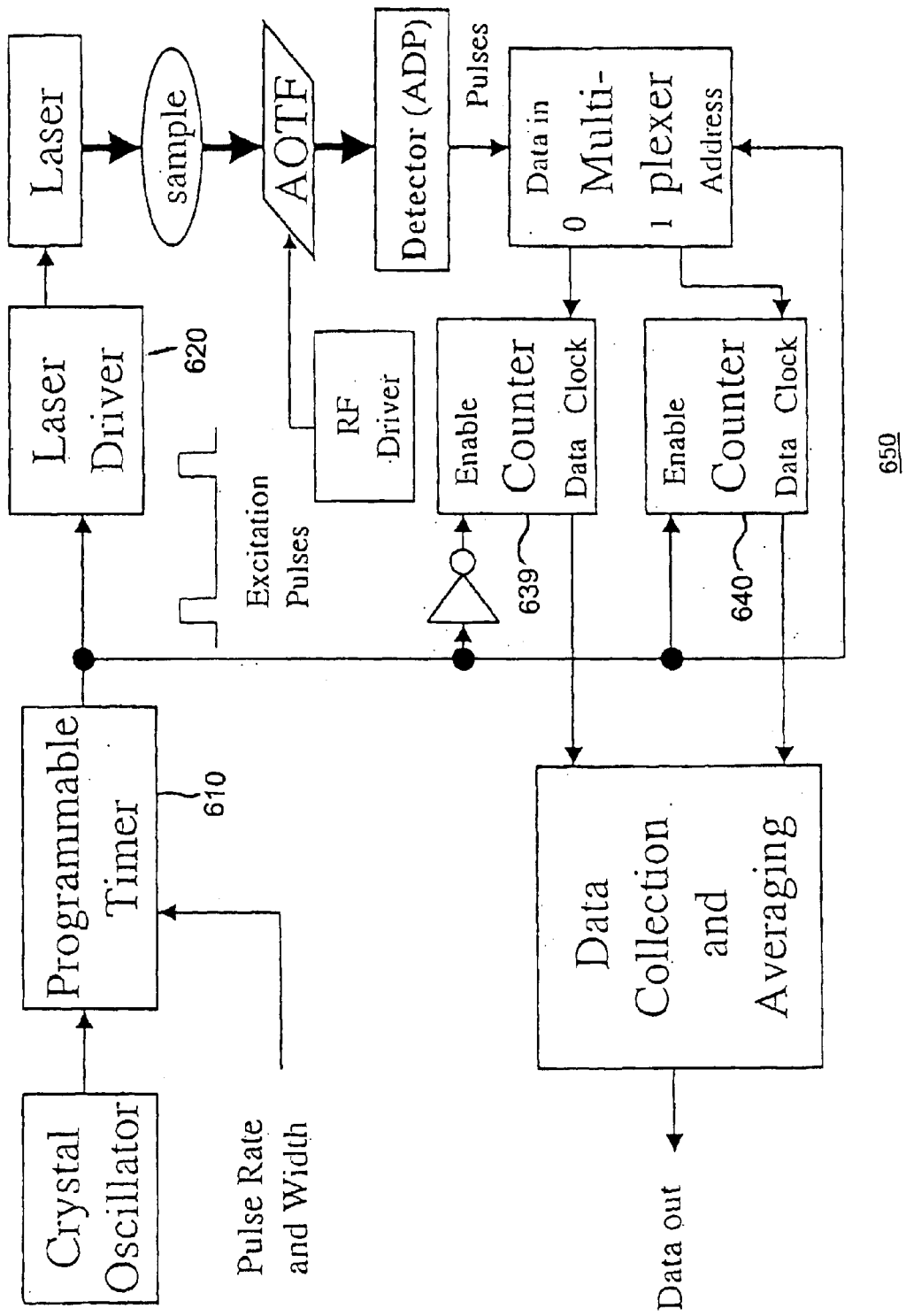
FIG. 6B is a block diagram of a pulsed excitation and gated detection system including a photon counting avalanche photodiode (APD) and digital techniques.

FIG. 6B shows an ITOS system 650 with pulsed excitation and gated detection using digital gated integration. System is similar to system 600 and uses the elements of system 600 to perform the function of system 570. Unlike system 600, the excitation is not a square wave, rather it is a sequence of pulses. Like system 570, this system provides gated integration. This is accomplished by gating on (enabling) the appropriate counter to receive pulses produced during excitation on or off times. FIG. 6B shows the same signal input to the laser driver 620 and the counter enable 640, but gate and delay generators (like 574 and 573 shown in FIG. 5C) could be added in between programmable timer 610 and counters 639 and 640.

Figure 6C:
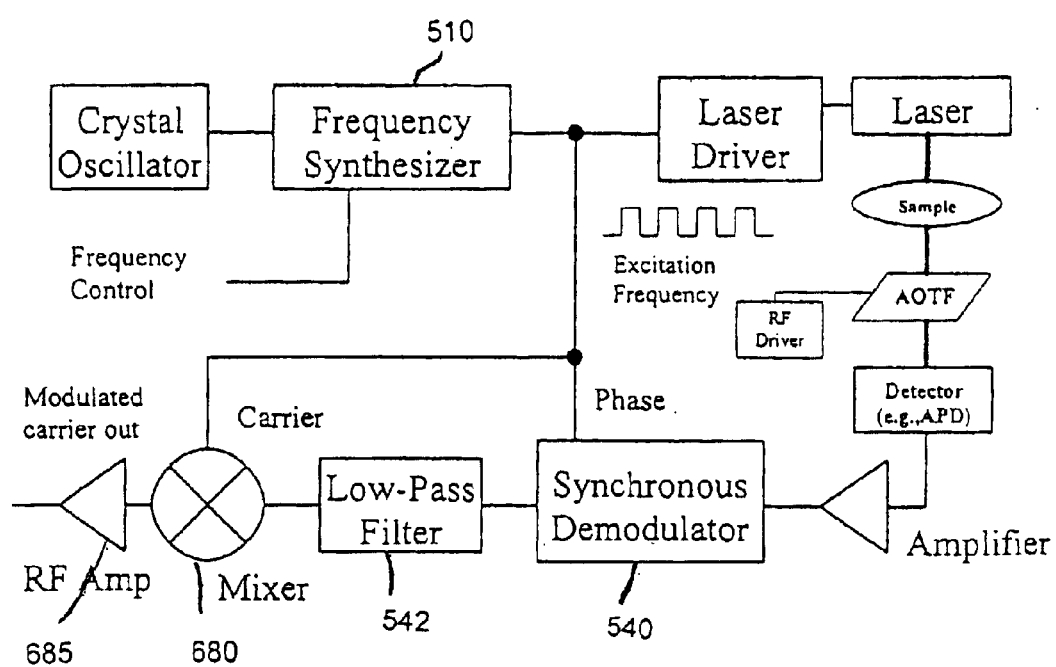
FIG. 6C is a block diagram of a modulated excitation and synchronous detection system with wireless RF data transmission

FIG. 6C shows a Wireless ITOS system 670 with modulated excitation, synchronous detection and RF data transmission. System 670 is analogous to system 500 shown in FIG. 5A, except ADC 545 in system 500 is replaced by mixer 680 and RF amplifier 685. Thus, in system 670, the detection signal is not digitized by the system, but is rather transmitted wirelessly using a radio-frequency (RF) link.

The RF carrier frequency can be the same as used the laser excitation for system 670 as shown in FIG. 6C. The detected signal coming output by synchronous demodulator 540 is then filtered by low-pass filter 542 to provide a low frequency (near dc) detection signal, which is used to modulate the RF carrier via mixer 680 as shown in FIG. 6C. The resulting modulated carrier signal is then amplified by the RF amplifier 685 and transmitted. A remotely located receiver (not shown) can demodulate the transmitted signal and extract the low-frequency Raman or other signal of interest for digitization and other data processing.

One advantage of ITOS technology is the ability to operate in the "slew scanning" mode. Slew scanning mode can vastly improve signal-to-noise values of measurements by concentrating on discrete and generally narrow spectral regions of interest. FIG. 7 shows the principle of slew scan mode applied to Raman spectroscopy. For example, a Raman spectrum of a compound usually covers wave numbers between about 2000 to 3000 $cm^{-1}$. However, generally only 2–5 peaks are sufficient to unambiguously identify the compound being interrogated. These Raman peaks are usually very narrow (less than 1 $cm^{-1}$) and depend on the spectral resolution of the instruments (5–10 $cm^{-1}$ for the Brimrose AOTFs used in Raman measurements). Therefore, if it is necessary to identify a specific compound in a complex mixture, it is only generally necessary to scan only a few (e.g. 2–3) narrow spectral regions where the Raman peaks are known to be located. The slew scan method can be applied to other emission spectra which generally exhibit a limited number of narrow emission peaks, such as atomic emission, atomic absorption, and atomic fluorescence.

FIG. 7(a) shows an exemplary Raman spectrum which includes a plurality of peaks. Assume that Raman peaks in each of the wave number ranges $\Delta va$, $\Delta vb$, and $\Delta vc$ can unambiguously identify a particular target. $\Delta va$, $\Delta vb$, and $\Delta vc$ are shown in FIG. 7(b) including respective peaks shown in FIG. 7(a). In contrast to the slew scan mode, in a conventional scan mode the entire spectral range from $v_o$ to $v_F$ is scanned at a constant rate.

A scanning tunable bandpass filter, such as a AOTF or LCTF can be programmed to slowly scan $\Delta va$, $\Delta vb$, and $\Delta vc$ regions (for example 10 $cm^{-1}$ each, or a total of only 30 $cm^{-1}$), which are rich in spectral information of interest. The scanning tunable bandpass filter can rapidly scan over other regions outside these narrow regions in the full range from $v_o$ to $v_F$. This method is referred to as the "slew scanning" mode and is unique to the present invention.

The slew scanning mode cannot be performed with multichannel detectors such as charge-coupled devices (CCDs) where the entire spectral regions must be collected. Thus, CCD based systems primarily produce meaningless data outside the spectral region(s) of interest. For example, to record an entire Raman spectrum using CCD devices, data must generally be recorded for the full 3000 $cm^{-1}$.

On the other hand, the slew scan method of the ITOS needs to only record data of 30 $cm^{-1}$, i.e. 100 times less data to record. Therefore the ITOS can be operated approximately 100 times faster then CCDs and obtain the most meaningful important information (e.g., data for 3 typical peaks). Alternatively, for the same measuring time, the ITOS can spend more time at the spectral region of interest (about 100 longer measuring time) in order to improve signal-to-noise values.

In an alternate embodiment, the ITOS can have a broader use. The slew scan scheme can be viewed as a "dynamic multi-element match filter" (DMMF) for a point-source or for a 2-dimensional image using multiple point sources. A DMMF comprises software that can be programmed and integrated into the system such that the device can search for a specific compound by scanning over a preselected combination of peaks characteristic of the compounds of interest.

The invention can be used in a wide variety of applications. For example, homeland defense, forensic and investigative, medical diagnostics, pharmaceutical, food, and agricultural product analysis, environmental bioremediation and monitoring, bioprocess monitoring and biotechnology applications.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

What is claimed is:

1. A scanning tunable detection system for analyzing a sample, comprising:
   a source of time varying excitation signals;
   diffractive optics for dividing a beam from said source of time varying excitation signal into a plurality of discrete excitation light beams which irradiate a plurality of locations on said sample;
   a tunable optical filter for selectively transmitting time-varying optical signals emanated from said sample following irradiation with said time varying excitation signals, and
   a detector array including a plurality of pixels for receiving a plurality of said time-varying optical signals emanated from said locations on said sample, said detector array for converting said plurality of time-varying optical signals to electrical detection signals.

2. The system of claim 1, wherein said tunable optical filter comprises an AOTF or a LCTF.

3. The system of claim 2, further comprising structure for modulating scanning of said AOTF.

4. The system of claim 1, further comprising a data treatment system for receiving said detection signals, said data treatment system providing at least one of phase-sensitive and time-sensitive detection.

5. The system of claim 4, wherein said excitation signals comprise pulses, said data treatment system including a time resolved module coupled to an output of said detector, said time resolved module only passing said electrical detection signals after a delay time sufficiently following said pulses so that a contribution from said excitation pulses in said electrical detection signal is substantially eliminated.

6. The system of claim 1, wherein said detector comprises at least one avalanche photodiode.

7. The system of claim 1, wherein said time-varying optical signals comprise Raman signals.

8. The system of claim 1, wherein said time-varying optical signals are selected from the group consisting of fluorescence signals, phosphorescence signals, and atomic emission signals.

9. The system of claim 1, further comprising a gated integrator for receiving said detection signals or signals derived from said detection signals, said gated integrator integrating said detection signals only after a predetermined period of time after said sample irradiation has ceased.

10. The system of claim 9, wherein a train of pulses are used to modulate said source of excitation signals, said train of pulses also applied to said gated integrator after said predetermined period of time.

11. The system of claim 1, further comprising a synchronous demodulator for receiving said time-varying electrical signals and a phase shift selector, wherein said phase shift selector synchronizes said synchronous demodulator to a modulation frequency applied to said excitation source.

12. The system of claim 1, further comprising a synchronous demodulator for receiving said time-varying electrical signals and a phase shift selector, wherein said phase shift selector synchronizes said synchronous demodulator to a modulation frequency applied to an output of said excitation source.

13. The system of claim 1, wherein said time varying excitation signals comprise a pulse train and said emanated signal is a series of pulses, further comprising a multiplexer for collecting said series of pulses and a first and second counter synchronized with said pulse train, said first counter for processing "0" states in said detection signals and said second counter for processing "1" states in said detection signals.

14. The system of claim 13, further comprising a data collection and averaging module connected to outputs of both said first and said second counter.

15. The system of claim 1, further comprising structure for wirelessly transmitting said detection signals.

16. A method for identifying at least one component in a sample, comprising the steps of:

providing a source of time-varying radiation;

irradiating said sample with said time-varying radiation, wherein a time-varying optical signal emanates from said sample, wherein said time-varying source provides a modulated frequency output, further comprising the step of synchronizing demodulation of said time-varying electrical signals with said modulated frequency;

converting said time-varying optical signals to electrical detection signals, and processing said electrical detection signals to provide time-varying measurements relating to said sample.

17. The method of claim 16, further comprising the step of selectively transmitting time-varying optical signals emanating from said sample.

18. The method of claim 17, wherein an AOTF or a LCTF provides said selective transmitting.

19. The method of claim 16, wherein said time varying measurements include lifetime determination.

20. The method of claim 19, wherein said time-varying measurements include time resolved measurements.

21. The method of claim 19, wherein said time-varying measurements include phase resolved measurements.

22. The method of claim 16, wherein said optical signals comprises Raman signals.

23. The method of claim 16, further comprising the step of delaying initiation of said converting step for a predetermined time after said irradiating.

24. The method of claim 16, wherein said processing comprises imaging said sample.

25. A method for identifying at least one component in a sample, comprising the steps of:

providing a source of time-varying radiation;

irradiating said sample with said time-varying radiation, wherein a time-varying optical signal emanates from said sample, wherein said irradiation step comprises slew scanning;

converting said time-varying optical signals to electrical detection signals, and processing said electrical detection signals to provide time-varying measurements relating to said sample.

* * * * *